(12) United States Patent
Taibi et al.

(10) Patent No.: US 10,072,552 B2
(45) Date of Patent: Sep. 11, 2018

(54) METHOD AND SYSTEM OF TESTING THE PROPER FUNCTIONING OF A CATALYZED PARTICULATE FILTER OF AN INTERNAL COMBUSTION ENGINE

(71) Applicant: GM GLOBAL TECHNOLOGY OPERATIONS LLC, Detroit, MI (US)

(72) Inventors: Cristian Taibi, Turin (IT); Francesco Siano, Givoletto (IT)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 148 days.

(21) Appl. No.: 15/172,510

(22) Filed: Jun. 3, 2016

(65) Prior Publication Data

US 2016/0356673 A1 Dec. 8, 2016

(30) Foreign Application Priority Data

Jun. 3, 2015 (GB) .................................. 1509638.1

(51) Int. Cl.
*F01N 11/00* (2006.01)
*G01N 15/06* (2006.01)
(Continued)

(52) U.S. Cl.
CPC ............ *F01N 11/007* (2013.01); *F01N 3/035* (2013.01); *F01N 9/002* (2013.01); *F01N 11/002* (2013.01); *F01N 13/0097* (2014.06); *G01M 15/104* (2013.01); *G01N 15/0656* (2013.01); *F01N 3/103* (2013.01); *F01N 2250/02* (2013.01); *F01N 2560/025* (2013.01); *F01N 2560/026* (2013.01); *F01N 2900/0416* (2013.01); *F01N 2900/0418* (2013.01); *F01N 2900/08* (2013.01); *F01N 2900/1402* (2013.01); *F01N 2900/1606* (2013.01); *F01N 2900/1621* (2013.01); *G01N 2015/0046* (2013.01);
(Continued)

(58) Field of Classification Search
CPC ..... G01M 15/104; F01N 11/007; F01N 9/002
See application file for complete search history.

(56) References Cited

U.S. PATENT DOCUMENTS

2005/0188681 A1   9/2005   Emi et al.
2006/0053772 A1   3/2006   Dou et al.
(Continued)

FOREIGN PATENT DOCUMENTS

JP        2009156106 A      7/2009

OTHER PUBLICATIONS

Great Britain Patent Office, Great Britain Search Report for Great Britain Application No. 1509638.1, dated Dec. 3, 2015.

*Primary Examiner* — Paul West
(74) *Attorney, Agent, or Firm* — Lorenz & Kopf, LLP

(57) ABSTRACT

A method of testing the proper functioning of a catalyzed particulate filter of an internal combustion engine during regeneration of the catalyzed particulate filter is disclosed. A first value of an oxygen concentration in an exhaust gas upstream of the catalyzed particulate filter and a second value of an oxygen concentration in the exhaust gas downstream of the catalyzed particulate filter is measured during regeneration. The difference between the first value and the second value is calculated and a malfunctioning of the catalyzed particulate filter is indicated when the calculated difference is below a predetermined threshold value thereof.

12 Claims, 2 Drawing Sheets

(51) Int. Cl.
  *G01M 15/10* (2006.01)
  *F01N 9/00* (2006.01)
  *F01N 3/035* (2006.01)
  *F01N 13/00* (2010.01)
  *G01N 15/00* (2006.01)
  *F01N 3/10* (2006.01)

(52) U.S. Cl.
  CPC ....... *G01N 2015/0084* (2013.01); *Y02T 10/24* (2013.01); *Y02T 10/47* (2013.01)

(56) References Cited

U.S. PATENT DOCUMENTS

| | | |
|---|---|---|
| 2011/0072788 A1 | 3/2011 | Ruona et al. |
| 2011/0219746 A1 | 9/2011 | Yezerets et al. |
| 2012/0216507 A1 | 8/2012 | Nieuwstadt |
| 2015/0275738 A1* | 10/2015 | Van Nieuwstadt .......................... B01D 46/0086 73/114.76 |

* cited by examiner

METHOD AND SYSTEM OF TESTING THE PROPER FUNCTIONING OF A CATALYZED PARTICULATE FILTER OF AN INTERNAL COMBUSTION ENGINE

CROSS-REFERENCE TO RELATED APPLICATION

This application claims priority to Great Britain Patent Application No. 1509638.1, filed Jun. 3, 2015, which is incorporated herein by reference in its entirety.

TECHNICAL FIELD

The present disclosure pertains to a method and a system of testing the proper functioning of a catalyzed particulate filter of an internal combustion engine, such as a Diesel engine of a motor vehicle.

BACKGROUND

It is known that an internal combustion engine of a motor vehicle is equipped with an aftertreatment system designed to change the composition of the exhaust gas in order to reduce the pollutant emissions. Some aftertreatment systems may include a particulate filter, for example a Diesel particulate filter (DPF) designed to trap diesel particulate matter or soot contained in the exhaust gas, and in particular a Catalyzed Diesel Particulate Filter (CDPF) having also a non-methane hydrocarbon oxidation function.

CDPF technology extends DPF technology by including an oxidation catalyst in association with a DPF. For example catalyzed diesel particulate filters have a filter media, i.e. a monolithic wall-flow substrate, coated with a catalyst in such a way to promote chemical reactions (i.e. oxidation reactions) among components of the exhaust gas, in particular non-methane hydrocarbons, at high temperatures. However, during the lifetime of the CDPF, the conversion efficiency of this component may not be constant but may decrease progressively due to ageing and/or poisoning effects. For this reason, it may happen that even if CDPF still traps the soot matter, its conversion efficiency may reach a level which makes it unsuitable to efficiently oxidize non-methane hydrocarbons, decreasing its contribution to the pollutant emission reduction.

SUMMARY

In view of the above, the present disclosure provides a simple, rational and rather inexpensive solution for identifying when a catalyzed particulate filter becomes unable to convert non-methane hydrocarbons or considerably decreases its non-methane hydrocarbon oxidation function, thereby allowing the adoption of countermeasures that can prevent the above mentioned side effects. An embodiment of the disclosure provides a method of testing the proper functioning of a catalyzed particulate filter of an internal combustion engine. A regeneration of the catalyzed particulate filter is performed. A first value of an oxygen concentration in an exhaust gas upstream of the catalyzed particulate filter and a second value of an oxygen concentration in the exhaust gas downstream of the catalyzed particulate filter are measured. The difference between the first value and the second value are calculated. A malfunctioning of the catalyzed particulate filter is identified, if the calculated difference is below a predetermined threshold value thereof.

This method is based on the fact that, if the oxidization efficiency of the catalyst which coats the filter media of the catalyzed particulate filter is poor or null, during a regeneration process of the particulate filter, oxygen concentration of the exhaust gas which crosses the catalyzed particulate filter substantially does not considerably decrease. By looking at the values of the oxygen concentration upstream and downstream of the catalyzed particulate filter, the proposed method represents a simple and reliable solution for identifying that the catalyzed particulate filter is unable to fulfill its non-methane hydrocarbon oxidation function or this function is not sufficiently performed.

According to an embodiment, the method may determine, during the regeneration, an amount of particulate trapped in the catalyzed particulate filter. When the determined amount gets smaller than a predetermined threshold value thereof, the measurement is started. In this way, the measurement of the calculated difference becomes more reliable and the entire method more efficient, because the measurement is performed when the catalyzed particulate filter is substantially empty and, therefore, undesired disturbances, due to the burning soot, are suppressed.

According to an embodiment of the present disclosure, the method may integrate the calculated difference over the predetermined period of time. This aspect of the solution may reduce the probability of false identifications, thereby improving the reliability of the testing method.

According to a further embodiment, the method may generate a signal perceivable by a driver, such as for example a visual signal, a sound, or other signal, if the malfunctioning is identified. In this way the driver may be informed of the malfunctioning of the catalyzed particulate filter and that a service intervention is needed.

According to an aspect of the present disclosure, the predetermined threshold value may be determined on the basis of a volumetric flow rate of the exhaust gas. In this way the threshold value of the calculated difference can change allowing the testing method to be efficiently performed also under transient operating conditions of the engine. In particular, it is observed that the value of calculated difference is proportional to the volumetric flow rate of the exhaust gas which crosses the catalyzed particulate filter.

According to another aspect of the present disclosure, the predetermined threshold value may be determined on the basis of engine speed and engine torque. In this way the threshold value of the calculated difference can change allowing the testing method to be efficiently performed also under transient operating conditions of the engine. In particular, it is observed that the value of calculated difference is proportional to the volumetric flow rate of the exhaust gas which crosses the catalyzed particulate filter and therefore depends on engine speed and engine torque.

The proposed solution may be carried out with the help of a computer program including a program-code for carrying out the method described above, and in the form of a computer program product including the computer program. The method can be also embodied as an electromagnetic signal modulated to carry a sequence of data bits which represent a computer program to carry out all steps of the method.

The present solution may be alternatively embodied as a system for testing the proper functioning of a catalyzed particulate filter included in an aftertreatment system of an internal combustion engine, wherein the aftertreatment system includes a first oxygen sensor upstream of the catalyzed particulate filter and a second oxygen sensor downstream of the catalyzed particulate filter, and wherein the system includes an electronic control unit configured to: perform a regeneration of the catalyzed particulate filter, measure a first value of an oxygen concentration in an exhaust gas upstream of the catalyzed particulate filter and a second value of an oxygen concentration in the exhaust gas downstream of the catalyzed particulate filter during the regeneration, calculate the difference between the first value and the second value, and identify a malfunctioning of the catalyzed particulate filter, if the calculated difference is below a predetermined threshold value thereof.

This embodiment achieves the same effects of the method described above particularly that of providing a simple and reliable solution for identifying that the catalyzed particulate filter is unable to fulfill its non-methane hydrocarbon oxidation function or this function is not sufficiently performed.

According to an aspect of the solution, the first oxygen sensor may include or may be a lambda sensor. As an alternative, the first oxygen sensor may include or may be a nitrogen oxide sensor. According to an aspect of the solution, the second oxygen sensor may include or may be a lambda sensor or a nitrogen oxide sensor. In this way, the measurement of the oxygen concentrations is more reliable and the entire method more efficient.

According to another aspect of the solution, the electronic control unit may be configured to determine, during the regeneration, an amount of particulate trapped in the catalyzed particulate filter, and start the measurement when the determined amount gets smaller than a predetermined threshold value thereof. In this way, the measurement of the calculated difference becomes more reliable and the entire method more efficient, in particular the measurement may be performed when the catalyzed particulate filter is substantially empty and, therefore, undesired disturbances, due to the burning soot, may be suppressed.

Another aspect of the solution may provide that the electronic control unit is configured to integrate the calculated difference over the predetermined period of time. This aspect of the solution may reduce the probability of false identifications, thereby improving the reliability of the testing method.

According to another aspect of the solution, the electronic control unit may be configured to generate a signal perceivable by a driver, such as for example a visual signal, a sound, or other signal, if the malfunctioning is identified. In this way the driver may be informed of the malfunctioning of the catalyzed particulate filter and that a service intervention is needed.

Another embodiment of the solution provides an apparatus for testing the proper functioning of a catalyzed particulate filter of an internal combustion engine. A processor, electronic control unit or other means performs a regeneration of the catalyzed particulate filter. A sensor, sensors, processor or other means measures a first value of an oxygen concentration in an exhaust gas upstream of the catalyzed particulate filter and a second value of an oxygen concentration in the exhaust gas downstream of the catalyzed particulate filter, during the regeneration. A processor, electronic control unit or other means calculates the difference between the first value and the second value, and identifies a malfunctioning of the catalyzed particulate filter, if the calculated difference is below a predetermined threshold value thereof. This embodiment achieves basically the same effects of the method described above, particularly which of providing a simple and reliable solution for identifying that the catalyzed particulate filter is unable to fulfill its non-methane hydrocarbon oxidation function or this function is not sufficiently performed.

According to an aspect of the solution, the apparatus may include a processor, electronic control unit or other means to determine an amount of particulate trapped in the catalyzed particulate filter during the regeneration, and starts measuring when the determined amount gets smaller than a predetermined threshold value thereof. In this way, the measurement of the calculated difference becomes more reliable and the entire apparatus more efficient, in particular the measurement may be performed when the catalyzed particulate filter is substantially empty and, therefore, undesired disturbances, due to the burning soot, may be suppressed.

According to an embodiment of the present disclosure, the apparatus may include a processor, electronic control unit or other means to integrate the calculated difference over the predetermined period of time. This aspect of the solution may reduce the probability of false identifications, thereby improving the reliability of the diagnosis of the catalyzed particulate filter conversion efficiency.

According to a further embodiment, the apparatus may include a processor, electronic control unit or other means to generate a signal perceivable by a driver, such as for example a visual signal, a sound, or other signal, if the malfunctioning is identified.

In this way the driver may be informed of the malfunctioning of the catalyzed particulate filter and that a service intervention is needed.

According to an aspect of the present disclosure, the apparatus may include a processor, electronic control unit or other means to determine the predetermined threshold value on the basis of a volumetric flow rate of the exhaust gas. In this way the threshold value of the calculated difference can change allowing the diagnostic method to be efficiently performed also under transient operating conditions of the engine. In particular, it is observed that the value of calculated difference is proportional to the volumetric flow rate of the exhaust gas which crosses the catalyzed particulate filter.

According to an another aspect of the present disclosure, the apparatus may include a processor, electronic control unit or other means to determine the predetermined threshold value may on the basis of engine speed and engine torque. In this way the threshold value of the calculated difference can change allowing the diagnostic method to be efficiently performed also under transient operating conditions of the engine. In particular, it is observed that the value of calculated difference is proportional to the volumetric flow rate of the exhaust gas which crosses the catalyzed particulate filter and therefore depends on engine speed and engine torque.

BRIEF DESCRIPTION OF THE DRAWINGS

The present disclosure will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

Figure 1:
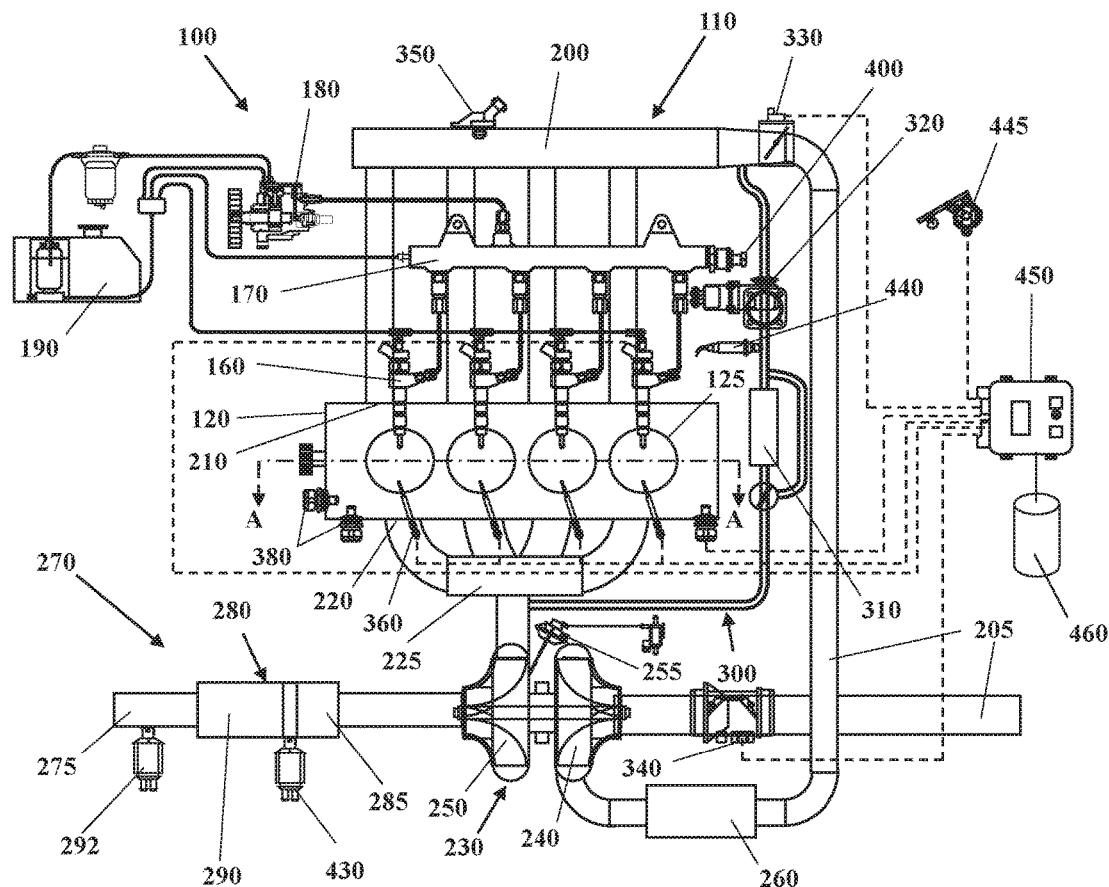
FIG. 1 shows an automotive system.
Figure 2:
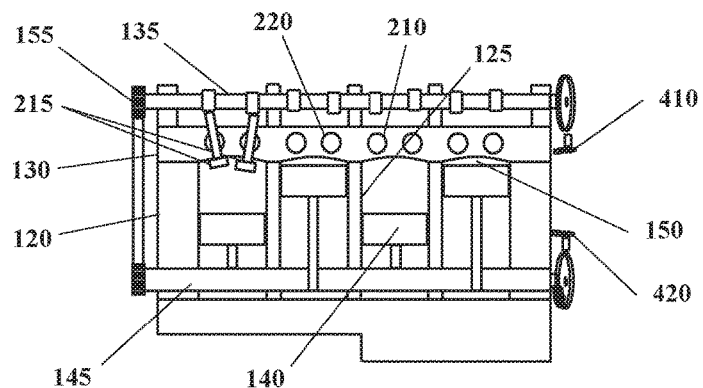
FIG. 2 is a cross-section of an internal combustion engine belonging to the automotive system of FIG. 1.

Some embodiments may include an automotive system 100, as shown in FIGS. 1 and 2, that includes an internal combustion engine (ICE) 110 having a cylinder block 120 defining at least one cylinder 125 having a piston 140 coupled to rotate a crankshaft 145. A cylinder head 130 cooperates with the piston 140 to define a combustion chamber 150.

A fuel and air mixture (not shown) is disposed in the combustion chamber 150 and ignited, resulting in hot expanding exhaust gasses causing reciprocal movement of the piston 140. The fuel is provided by at least one fuel injector 160 and the air through at least one intake port 210. The fuel is provided at high pressure to the fuel injector 160 from a fuel rail 170 in fluid communication with a high pressure fuel pump 180 that increase the pressure of the fuel received from a fuel source 190.

Each of the cylinders 125 has at least two valves 215, actuated by a camshaft 135 rotating in time with the crankshaft 145. The valves 215 selectively allow air into the combustion chamber 150 from the intake port 210 and alternately allow exhaust gases to exit through an exhaust port 220. In some examples, a cam phaser 155 may selectively vary the timing between the camshaft 135 and the crankshaft 145.

The air may be distributed to the air intake port(s) 210 through an intake manifold 200. An air intake duct 205 may provide air from the ambient environment to the intake manifold 200. In other embodiments, a throttle valve 330 may be provided to regulate the flow of air into the intake manifold 200. In still other embodiments, a forced air system such as a turbocharger 230, having a compressor 240 rotationally coupled to a turbine 250, may be provided. Rotation of the compressor 240 increases the pressure and temperature of the air in the air intake duct 205 and intake manifold 200. An intercooler 260 disposed in the air intake duct 205 may reduce the temperature of the air.

The turbine 250 rotates by receiving exhaust gases from an exhaust manifold 225 that directs exhaust gases from the exhaust ports 220 and through a series of vanes prior to expansion through the turbine 250. The exhaust gases exit the turbine 250 and are directed into an exhaust gas aftertreatment system 270. This example shows a variable geometry turbine (VGT) 250 with a VGT actuator 255 arranged to move the vanes to alter the flow of the exhaust gases through the turbine 250.

The exhaust gas aftertreatment system 270 may include an exhaust gas line 275 having one or more exhaust aftertreatment devices 280. The aftertreatment devices 280 may be any device configured to change the composition of the exhaust gases. Some examples of aftertreatment devices 280 include, but are not limited to, catalytic converters (two and three way), oxidation catalysts, for example a Diesel Oxidation Catalyst (DOC) 285, lean NOx traps, hydrocarbon adsorbers, selective catalytic reduction (SCR) systems, and particulate filters, in particular a Catalyzed Diesel Particulate Filter (CDPF) 290 located in the exhaust line 275 downstream of the DOC 285.

Other embodiments may include an exhaust gas recirculation (EGR) duct 300 coupled between the exhaust manifold 225 and the intake manifold 200. The EGR duct 300 may include an EGR cooler 310 to reduce the temperature of the exhaust gases in the EGR duct 300. An EGR valve 320 regulates a flow of exhaust gases in the EGR duct 300.

The automotive system 100 may further include an electronic control unit (ECU) 450 in communication with one or more sensors and/or devices associated with the ICE 110. The ECU 450 may receive input signals from various sensors configured to generate the signals in proportion to various physical parameters associated with the ICE 110. The sensors include, but are not limited to, a mass airflow, pressure, temperature sensor 340, a manifold pressure and temperature sensor 350, a combustion pressure sensor 360, coolant and oil temperature and level sensors 380, a fuel rail pressure sensor 400, a cam position sensor 410, a crank position sensor 420, exhaust pressure and temperature sensors 430, an EGR temperature sensor 440, an accelerator pedal position sensor 445, and oxygen concentration sensors 291,292, such as a first oxygen concentration sensor 291 located in the exhaust line 275 upstream of the CDPF 290, for example between the DOC 285 and the CDPF 290 (see FIG. 3) or upstream of the DOC 285 (see FIG. 4), and a second oxygen concentration sensor 292 located in the exhaust line 275 downstream of the CDPF 290. For example each of the oxygen concentration sensors 291,292 may be a lambda sensor or a NOx sensor.

Furthermore, the ECU 450 may generate output signals to various control devices that are arranged to control the operation of the ICE 110, including, but not limited to, the fuel injector 160, the throttle valve 330, the EGR Valve 320, the VGT actuator 255, the waste gate actuator 252 and the cam phaser 155. Note, dashed lines are used to indicate communication between the ECU 450 and the various sensors and devices, but some are omitted for clarity.

Turning now to the ECU 450, this apparatus may include a digital central processing unit (CPU) 460 in communication with a memory system and an interface bus. The CPU 460 is configured to execute instructions stored as a program in the memory system, and send and receive signals to/from the interface bus. The memory system may include various storage types including optical storage, magnetic storage, solid state storage, and other non-volatile memory. The interface bus may be configured to send, receive, and modulate analog and/or digital signals to/from the various sensors and control devices. The program may embody the methods disclosed herein, allowing the CPU 460 to carryout out various methods and control the ICE 110.

The program stored in the memory system is transmitted from outside via a cable or in a wireless fashion. Outside the automotive system 100 it is normally visible as a computer program product, which is also called computer readable medium or machine readable medium in the art, and which should be understood to be a computer program code residing on a carrier, the carrier being transitory or non-transitory in nature with the consequence that the computer program product can be regarded to be transitory or non-transitory in nature.

An example of a transitory computer program product is a signal, e.g. an electromagnetic signal such as an optical signal, which is a transitory carrier for the computer program code. Carrying such computer program code can be achieved by modulating the signal by a conventional modulated technique such as QPSK for digital data, such that binary data representing the computer program code is impressed on the transitory electromagnetic signal. Such signals are e.g. made use of when transmitting computer program code in a wireless fashion via a WiFi connection to a laptop.

In case of a non-transitory computer program product the computer program code is embodied in a tangible storage medium. The storage medium is then the non-transitory carrier mentioned above, such that the computer program code is permanently or non-permanently stored in a retrievable way in or on this storage medium. The storage medium can be of conventional type known in computer technology such as a flash memory, an Asic, a CD or the like.

Instead of an ECU 450, the automotive system 100 may have a different type of processor to provide the electronic logic, e.g. an embedded controller, an onboard computer, or any processing module that might be deployed in the vehicle.

One of the tasks of the ECU 450 may be that of performing a regeneration process of the CDPF 290, when the amount of particulate matter accumulated therein exceeds a first predetermined threshold value thereof. The regeneration process generally provides for the ECU 450 to increase the temperature of the CDPF 290 up to a temperature (e.g. 630° C.) that causes the accumulated particulate matter to burn off. For example, to achieve this temperature increase, the ECU 450 may be configured to command the fuel injector 160 to operate so-called post injections, namely to inject small quantities of fuel into the combustion chambers 150 during the exhaust stroke of piston 140, when the exhaust port 220 is already open. In this way the post injected fuel quantities exit unburnt the combustion chambers 150 and reach the DOC 285 and the CDPF 290, where they are ignited and generate a stream of hot exhaust gas that is able to increase the temperature of the CDPF 290.

The ECU 450 may provide to stop the regeneration process when the amount of particulate matter accumulated therein gets smaller than a second predetermined threshold value thereof, smaller than the first predetermined threshold value. In particular, the second predetermined threshold value should be indicative of the fact that the CDPF 290 is substantially empty and its original trapping efficiency are restored.

The ECU 450 may be further configured to execute a diagnostic strategy aimed to identify whether the conversion efficiency of CDPF 290 is high enough. In particular, the ECU 450 is configured to execute this diagnostic strategy when the CDPF 290 is substantially empty or at least when the amount of particulate matter accumulated into the CDPF 290 becomes smaller than the second predetermined threshold value. According to this aspect, the diagnostic strategy may not be influenced or disturbed by the particulate matter (carbon) trapped in the CDPF 290. This diagnostic strategy may be based on the fact that, if the oxidization efficiency of a catalyst which coats a filter media of the CDPF 290 is poor or null, the oxygen concentration of the exhaust gas which crosses the CDPF 290 does not considerably decrease passing through the CDPF 290.

Based on this consideration, the diagnostic strategy provides that the ECU 450 operates the ICE 110 so as to perform a regeneration process of the CDPF 290 according to the procedure that has been explained above (block S1). Moreover, while the regeneration process is underway, the ECU 450 determines the amount of particulate matter accumulated into the CDPF 290 and, when the amount of particulate matter gets smaller than the second predetermined threshold value, the ECU 450 commands an extension, for a predetermined period of time, of the regeneration process. This predetermined period of time may be a calibration parameter and may be for example one minute long.

In practice, even if the CDPF 290 is substantially empty (e.g. the amount of particulate matter lower than the second threshold value thereof), the ECU 450 commands to continue the regeneration process till that predetermined period of time will end. In this way, during the predetermined period of time, a determined amount of non-methane hydrocarbons is still fed through the aftertreatment devices 280, and in particular through the CDPF 290. While the predetermined period of time of the extended regeneration process is underway, the diagnostic strategy provides for the ECU 450 to determine (block S2) a first value $O_2'$ of the oxygen concentration along the exhaust line 275 upstream of the CDPF 290, for example between the DOC 285 and the CDPF 290, and to determine a second value $O_2''$ (block S3) of the oxygen concentration along the exhaust line 275 downstream of the CDPF 290. In particular, the first value $O_2'$ may be measured by means of the first oxygen concentration sensor 291 and the second value $O_2''$ may be measured by means of the second oxygen concentration sensor 292.

The diagnostic strategy further provides for the ECU 450 to filter (blocks S4 and S5) the measured first value $O_2'$ and second value $O_2''$ and to calculate (block S6) a difference $\Delta O_2$ between the filtered first value $O_2'$ and the filtered second value $O_2''$. Again, the diagnostic strategy may provide for the ECU 450 to integrate (block S7) the calculated difference $\Delta O_2$ over the predetermined period of time, in order to determine an oxygen amount consumed into the CDPF 290 due to the oxidation reactions occurring therein, during the predetermined period of time. The diagnostic strategy may also provide for the ECU 450 to compare (block S8) the integrated difference $\Delta O_2$ with a threshold value $O_2^{th}$. The threshold value $O_2^{th}$ may be indicative l| of the fact that, during the predetermined period of time, oxidation reactions of the non-methane hydrocarbons contained in the exhaust gas, with oxygen consumption, inside the CDPF 290 are occurring. To a certain extent the threshold value $O_2^{th}$ (or the calculated difference $\Delta O_2$) may depend on a volumetric flow rate of the exhaust gas. As a matter of fact, the volumetric flow rate of the exhaust gas is a physical parameter affecting oxygen consumption across the CDPF 290. For this reason, the ECU 450 may be configured to determine current values of the volumetric flow rate of the exhaust gas through the CDPF 290 and to use them to determine a current corresponding threshold value $O_2^{th}$. By way of example, the threshold value $O_2^{th}$ may be retrieved from a calibration map stored in the memory system.

The volumetric flow rate of the exhaust gas through the CDPF 290 may be estimated on the basis of the engine working points (namely, engine speed and engine torque) and the position of the EGR valve 320. In case no exhaust gas recirculation is applied during diagnostic operation in the regeneration process of the CDPF 290, to a certain extent the threshold value $O_2^{th}$ (or the calculated difference $\Delta O_2$) may depend on the engine operating conditions, namely on the engine speed and on the engine torque. For this reason, the ECU 450 may be configured to determine the current values of the engine speed and of the engine torque and to use them to determine a current corresponding threshold value $O_2^{th}$. By way of example, the threshold value $O_2^{th}$ may be retrieved from a calibration map stored in the memory system.

Figure 3:
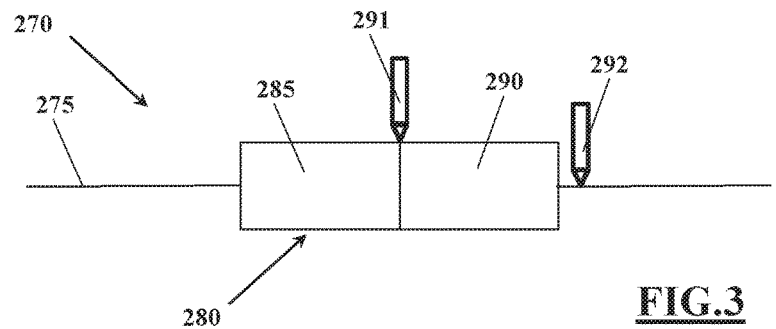
FIG. 3 is a schematic view of an exhaust gas aftertreatment system according to an embodiment of the present solution.
Figure 4:
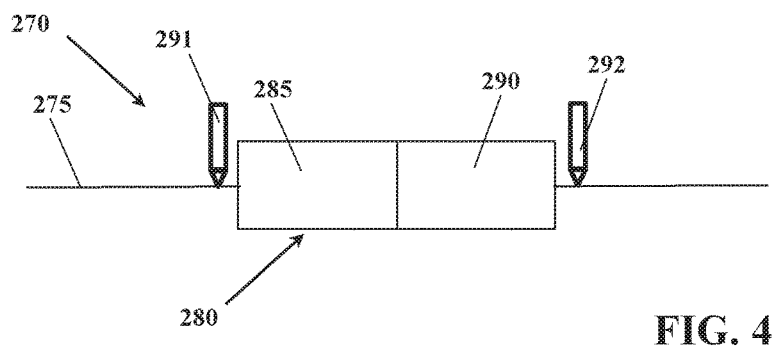
FIG. 4 is a schematic view of an exhaust gas aftertreatment system according to a further embodiment of the present solution.
Figure 5:
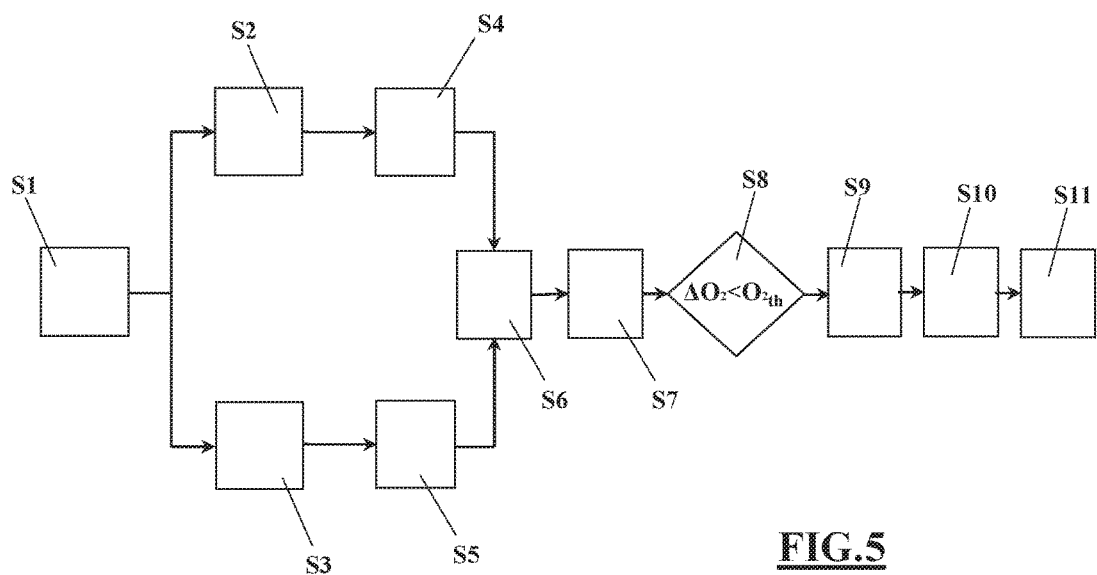
FIG. 5 is a flowchart representing a strategy of diagnosing a malfunctioning of a catalyzed particulate filter.

Again, to a certain extent the threshold value $O_2^{th}$ may depend on the position of the first oxygen concentration sensor 291 along the exhaust gas line 275. In particular, threshold value $O_2^{th}$ may be different whether the first oxygen concentration sensor 291 is disposed between the DOC 285 and the CDPF 290 (as shown in FIG. 3) or upstream of the DOC 285 (as shown in FIG. 4), in this latter case the threshold value $O_2^{th}$ should take account of a further contribution of oxygen consumption representative of the conversion efficiency of the DOC 285.

If the integrated difference $\Delta O_2$ is smaller than the threshold value $O_2^{th}$ (block S9), i.e. the oxygen amount subtracted from the exhaust gas into the GMT 290 due to the oxidation reactions occurring therein—during the predetermined period of time—is so small to be indicative of a unsatisfactory conversion efficiency of the GMT 290, an anomalous condition is met that leads the ECU 450 to identify that a malfunctioning of the CDPF 290 is occurring (block S10). In this case, a malfunctioning means that the CDPF 290 does not properly function as expected in its non-methane hydrocarbon oxidation function, for example a malfunctioning is identified when no or few (less than expected) oxidation of non-methane hydrocarbon occurs in the CDPF 290.

Once a malfunctioning of the CDPF 290 has been identified, the ECU 450 may be configured to perform one or more recovery actions (block S11). These recovery actions may include, but are not limited to, the generation of a signal perceivable by a driver, for example through the activation of an indicator (e.g. a light) disposed in a dashboard of the automotive system 100. In this way the driver may be informed of the malfunctioning of the CDPF 290 and suggested to take some countermeasures, for example to go to the nearest car service center.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

What is claimed is:

1. A method of function testing a catalyzed particulate filter of an internal combustion engine, comprising:
    regenerating the catalyzed particulate filter;
    determining an amount of particular trapped in the catalyzed particulate filter during the regeneration and, when the determined amount of particulate trapped in the catalyzed particulate filter is less than a first, predetermined value,
    measuring a first value of an oxygen concentration in an exhaust gas upstream of the catalyzed particulate filter during the regeneration;
    measuring a second value of an oxygen concentration in the exhaust gas downstream of the catalyzed particulate filter during the regeneration; and
    identifying a malfunctioning of the catalyzed particulate filter when a difference between the first value and the second value is less than a second, predetermined threshold value.

2. The method according to claim 1, further comprising integrating the difference over a predetermined period of time.

3. The method according to claim 1, further comprising generating a signal perceivable by a driver when the malfunctioning is identified.

4. The method according to claim 1, wherein the second, predetermined threshold value is determined on the basis of a volumetric flow rate of the exhaust gas.

5. The method according to claim 1, wherein the second, predetermined threshold value is determined on the basis of engine speed and engine torque.

6. A system for function testing a catalyzed particulate filter in an aftertreatment system of an internal combustion engine, comprising:
    a first oxygen sensor upstream of the catalyzed particulate filter;
    a second oxygen sensor downstream of the catalyzed particulate filter; and wherein
    an electronic control unit configured to:
        perform a regeneration of the catalyzed particulate filter;
        determine an amount of particulate trapped in the catalyzed particulate filter during the regeneration and, when the determined amount is less than a first, predetermined threshold value, receive a first signal from the first oxygen sensor to measure a first value of an oxygen concentration in an exhaust gas upstream of the catalyzed particulate filter during the regeneration and receive a second signal from the second oxygen sensor to measure and a second value of an oxygen concentration in the exhaust gas downstream of the catalyzed particulate filter during the regeneration; and
        identify a malfunctioning of the catalyzed particulate filter when a calculated difference between the first value and the second value is less than a second, predetermined threshold value thereof.

7. The system according to claim 6, wherein the first oxygen sensor comprises a lambda sensor.

8. The system according to claim 6, wherein the first oxygen sensor comprises a nitrogen oxide sensor.

9. The system according to claim 6, wherein the second oxygen sensor comprises a lambda sensor.

10. The system according to claim 6, wherein the second oxygen sensor comprises a nitrogen oxide sensor.

11. The system according to claim 6, wherein the electronic control unit is configured to integrate the calculated difference over a predetermined period of time.

12. The system according to claim 6, further comprising an indicator perceivable by a driver, wherein the electronic control unit is configured to activate the indicator when the malfunctioning is identified.

* * * * *